(12) United States Patent
Chiang et al.

(10) Patent No.: US 6,933,416 B2
(45) Date of Patent: Aug. 23, 2005

(54) PROCESS FOR THE PRODUCTION OF BISPHENOL-A

(75) Inventors: Chen-Chou Chiang, Wexford, PA (US); David L. Fair, Imperial, PA (US)

(73) Assignee: Calgon Carbon Corporation, Pittsburgh, PA (US)

( * ) Notice: Subject to any disclaimer, the term of this patent is extended or adjusted under 35 U.S.C. 154(b) by 0 days.

(21) Appl. No.: 10/412,180

(22) Filed: Apr. 11, 2003

(65) Prior Publication Data

US 2004/0019241 A1 Jan. 29, 2004

Related U.S. Application Data

(63) Continuation-in-part of application No. 10/207,585, filed on Jul. 29, 2002.

(51) Int. Cl.⁷ .............................................. C07C 39/16
(52) U.S. Cl. ........................................ 568/728
(58) Field of Search .......................... 568/728

(56) References Cited

U.S. PATENT DOCUMENTS

| | | |
|---|---|---|
| 4,391,997 A | 7/1983 | Mendiratta |
| 4,400,555 A | 8/1983 | Mendiratta |
| 4,522,726 A | 6/1985 | Berry et al. |
| 4,569,371 A | 2/1986 | Dolejs et al. |
| 4,612,022 A | 9/1986 | Berry |
| 4,704,262 A | 11/1987 | Berry |
| 4,764,276 A | 8/1988 | Berry et al. |
| 4,808,317 A | 2/1989 | Berry et al. |
| 5,087,767 A | 2/1992 | Okamoto et al. |
| 5,405,992 A | 4/1995 | Funk et al. |
| 5,502,248 A | 3/1996 | Funk et al. |
| 5,618,972 A | 4/1997 | Funk et al. |
| 5,676,826 A | 10/1997 | Rossiter et al. |
| 5,679,312 A | 10/1997 | Jin et al. |
| 6,114,577 A | 9/2000 | Verhoff et al. |
| 6,431,202 B1 | 8/2002 | Ahlgren et al. |
| 6,576,137 B1 | 6/2003 | Ma |
| 2003/0094416 A1 | 5/2003 | Heikkila et al. |

FOREIGN PATENT DOCUMENTS

| | | |
|---|---|---|
| EP | 1 116 508 A1 | 7/2001 |
| JP | 11228455 | 8/1999 |
| WO | WO 03/026772 A2 | 4/2003 |

OTHER PUBLICATIONS

M. Kawase, T.B. Suzuki, K. Inoue, K. Yoshimoto, K. Hashimoto, Chem. Eng. Sci., vol. 51, 2971–2976 (1996).
Kawase, M.; Inoue, Y.; Araki, K.; Hashimoto, K. Catalyst Today 1999, 48, 199–209.
M. Mazzotti, A. Kruglove, B. Neri, D. Gelosa, M. Morbidelli, Chem. Eng. Sci. vol. 51,1827–1836 (1996).
Ray A., Tonkovich, A.L. Aris, R., Carr, R. W., Chem. Eng. Sci., vol. 45, No. 8 2431–2437 (1990).
A.V. Kruglov, M.C. Bjorklund, R.W. Carr, Chem. Eng. Sci., vol. 51, 2945–2950 (1996).
Motoaki Kawase, Yasunobu Inoue, Takushi Araki, Kenji Hashimoto, "The simulated moving–bed reactor for production of bisphenol A," Catalysis Today 48 (1999) 199–109.

*Primary Examiner*—Paul A. Zucker
(74) *Attorney, Agent, or Firm*—Christine W. Trebilcock, Esq.; Cohen & Grigsby, P.C.

(57) ABSTRACT

The invention provides a process for the continuous production of bisphenol-A by continuously reacting phenol using an acid catalyst resin and continuously or essentially continuously removing water from the system. Continuous removal of water allows for increased catalytic activity of the resin and therefore improved productivity. Removal is facilitated by conducting the process in a carousel simulated moving bed device. Process efficiency is further enhanced by conducting the process in a device configured to have a combination of series, parallel or reverse flows which are optionally arranged so the process results in higher yield and lower impurities.

18 Claims, 2 Drawing Sheets

PROCESS FOR THE PRODUCTION OF BISPHENOL-A

CROSS REFERENCE

This application is a continuation-in-part of U.S. patent application Ser. No. 10/207,585 filed on Jul. 29, 2002.

FIELD OF INVENTION

This invention relates to a process for preparing bisphenol-A by continuously reacting phenol with acetone using a heterogeneous acid catalyst resin and continuously removing water from the system.

BACKGROUND OF THE INVENTION

Bisphenol-A ("BPA") is an important starting material for the production of polycarbonate plastics and epoxy resins. It is most often produced by the acid catalyzed condensation of phenol with acetone by the following reaction:

2 Phenol+Acetone→Bisphenol A+Water

While a homogenous acid catalyst such as hydrogen chloride has been used for many years, heterogeneous catalyst systems have become the more popular technique for producing BPA. Most of the heterogeneous catalysts are sulfonated polystyrene ion exchange resins. These catalysts provide a number of advantages. They are non-corrosive and easily separated from the reaction mixture. The catalysts work with continuous processes such as continuous fixed bed technology which uses a fixed bed reactor. For example, a phenol/acetone mixture is continuously fed through a bed of a heterogeneous catalyst ion exchange resin and, at steady state, water is constantly generated from the reaction and removed with the continuous flow of phenol through the resin bed. The desired BPA product is then collected by crystallization and further purified by recrystallization.

A well-known drawback of this technology is that the by-product water greatly reduces the activity of the resin catalyst. This is because the water strongly hydrates the acid groups, thus competing for these sites with the reactants. As the amount of water adsorbed on the catalytic sites increases the resin activity decreases. Without some means for removal of the water, the activity of the resin catalyst becomes unacceptably slow. As a result of this inhibition, BPA reactors can require higher resin volumes adding to the cost of the BPA plant. Co-catalysts can be used to boost the reaction rate, adding to the catalyst cost. Higher temperatures can be used to achieve the desired productivity thus leading to increased by-product formation.

Over the years, researchers have tried to solve the water inhibition problem by developing reaction systems that continuously remove the reaction water from the reaction zone. U.S. Pat. No. 5,087,767 describes a reaction system in which pervaporation is used to continuously remove water from the reactor. The process utilizes a membrane (organic or ceramic) permeable to water but not to acetone, phenol, and BPA. More recently, U.S. Pat. No. 5,679,312 describes a reactive/stripping process for continuously stripping water from a BPA reactor. The reactor consists of a multi-stage distillation column. One of the drawbacks to this technology is that it requires the use of a nitrogen stream to strip the water from the reaction liquid.

The traditional simulated moving bed ("SMB") process is one where a plurality of beds packed with solid media are used to carry out a continuous separation. The beds are connected endlessly in series with a unidirectional fluid flow through the system. Each bed is fitted with inlet and outlet ports that are switched on and off to create a simulated movement of the solid. The liquid flow combined with the simulated counter current solid movement results in the separation of components that have different affinities for the solid media. If a reaction is added to the system, a continuous reaction/separation system is created. For a general review of SMB technology, see Preparative and Production Scale Chromatography, Ganetsos, G., Barker, P. E., Eds.; Chromatographic Science Series Vol. 61; Marcel Dekker Inc.: New York, 1993; Chapters 12–13.

Recently, one group of researchers has investigated the potential for using an SMB device for carrying out the BPA reaction, which is described in The Simulated Moving-Bed Reactor for Production of Bisphenol A, Kawase, M.; Inoue, Y.; Araki, K.; Hashimoto, K.; Catalysis Today, Vol. 48, p. 199–209 (1999). Based upon laboratory adsorption and kinetic data they conducted a numerical simulation of a SMB process. Although they hypothesized that SMB could be suitable for the production of BPA, no experiments were conducted to confirm the predictions of the simulation. There is no discussion about the generation of impurities or the advantages that can be realized through use of non-traditional SMB flow configurations.

Accordingly, it is an object of an embodiment of the present invention to provide an efficient process for production of BPA. Therein water is continuously drawn off to reduce the adverse affects of water on the process reaction, and overcome disadvantages of water inhibition including its requirements for high reaction temperatures, large reactor volumes or use of co-catalysts. In another embodiment, it is a object of the invention to provide a process for producing BPA that can be used on a commercial scale.

SUMMARY OF THE INVENTION

In general, the present invention provides a process for the continuous production of bisphenol-A that comprises reacting phenol with acetone using an acid catalyst resin, and removing water from the process reaction. Simultaneously or sequentially as the phenol reacts with acetone, the water is removed continuously or essentially continuously using a continuous reaction/separation device to allow for higher catalytic activity of the resin. The reaction may be continuous for so long as reactant is present. The device preferably contains a plurality of beds or columns containing acid catalyst resin and being moveably connected serially or parallel to another column, i.e., connected in a series configuration, in a carousel, to simulate a resin flow. Preferably, the High Performance Carousel Simulated Moving Bed ("HPC-SMB") device available from Calgon Carbon Corporation is used.

The columns are arranged to provide appropriate zones for elution, enrichment and reaction stages of the process. The acetone is fed into two or more columns in the reaction zone. In the water elution zone, adsorbed water is removed from the resin with either phenol or another solvent. If a solvent other than phenol is used to remove water from the resin it will have to be regenerated and recycled to the elution zone. If phenol is used, enough makeup phenol is added to the elution zone to both dehydrate the resin and to provide enough excess phenol for the reaction zone. Downstream of the reaction zone, the crude BPA product as well as excess phenol are extracted from the process. A portion of the extracted product can optionally be passed to a reload zone to recover phenol from the resin bed for reuse.

In one embodiment, the process is conducted using columns connected in a series flow configuration having a unidirectional fluid flow through the system. In an embodiment, the process uses a carousel SMB reactor. Each column is fitted with inlet and outlet ports that are switched on and off to create a simulated movement of the acid catalyst resin. The acid catalyst resin is a heterogeneous catalyst. Conducting the process in a series configuration matches process performance of traditional SMB and exceeds the performance of a continuous fixed bed reactor because continuous removal of the water yields higher productivity.

Another embodiment of the process employs unique flow configurations with a carousel SMB to advantageously result in higher yield and lower impurities. The product water is simultaneously removed from the reaction by the simulated countercurrent movement of the resin bed against the flow of the reaction mixture. Particularly the HPC-SMB is configured to provide a flow configuration that is significantly different from the traditional SMB. Alternative flow configurations such as parallel flow and reverse flow can be advantageously used to increase productivity and reduce the formation of by-products. In an example, the process employs a parallel flow to allow for dilution of the reactant, thereby reducing the formation of by-products that result from the reaction of the reactant with itself. The reverse flow (up-flow) prevents pressure build up in the unit by allowing the resin to expand rather than simply swell in place and constrict the fluid flow. This leads to increased productivity by reducing down time.

In an example, the columns contain a solid or mixture of solids that act as a catalyst for the desired reaction and an adsorbent or separation media for removing the reaction product or other desired components. There are a wide variety of solid catalysts and adsorbents available. These materials generally applied for catalysis and/or separation include, but are not limited to, activated carbon, silica gels, aluminas, zeolites, zirconias, titanias, silicates, diatomaceous earths, and ion exchange resins. In one embodiment, a solid is used where it sufficiently performs both the catalytic and adsorbent functions. In an example using two or more solids, one performs the catalytic function while the other performs the separation function. These materials are chosen to provide enhanced reaction and separation over a single material. Also, it is possible to select a solid resin that acts only as a separation medium while the catalyst is not part of the solid phase but rather is dissolved in the liquid phase. In an embodiment for producing BPA, the solid catalyst and adsorbent is an ion exchange resin.

In an example of the process of the invention one or more eluents are used to selectively desorb the reaction products, byproducts, or contaminant from the bed using an isocratic elution or a gradient elution process. The eluent comprises or contains a liquid capable of displacing such reaction product, byproduct, or contaminant from the adsorption bed. Examples of eluents include, for example, alcohols, ketones, esters, aliphatic hydrocarbons, aromatic hydrocarbons, amides, nitrites, water, or buffered solutions. Mixtures of eluents may also be used. The preferred eluent for BPA is phenol.

Other features, aspects and advantages of the present invention will become better understood or apparent from a perusal of the following detailed description and examples of the invention and appended claims.

DESCRIPTION OF EXAMPLES OF THE INVENTION

The present invention provides a process for the continuous production of BPA comprising reacting phenol with acetone using an acid catalyst resin and continuously or essentially continuously removing water from the reaction. This reaction and separation process is conducted in multiple columns comprised of a solid or mixture of solids connected in series, parallel, or combination of such configurations. The reaction/separation can occur concurrently or sequentially. Each column can be independently operated with a liquid flow direction that runs from the top of the column to the bottom of the column or from the bottom of the column to the top of the column (reverse flow). A more detailed description of the variety of flow configurations can be found in applicants' application entitled High Performance Continuous Reaction/Separation Process Using A Continuous Liquid-Solid Contactor Ser. No. 10/207,585 that is being filed simultaneously herewith. The columns move or rotate to simulate a media flow.

Figure 1:
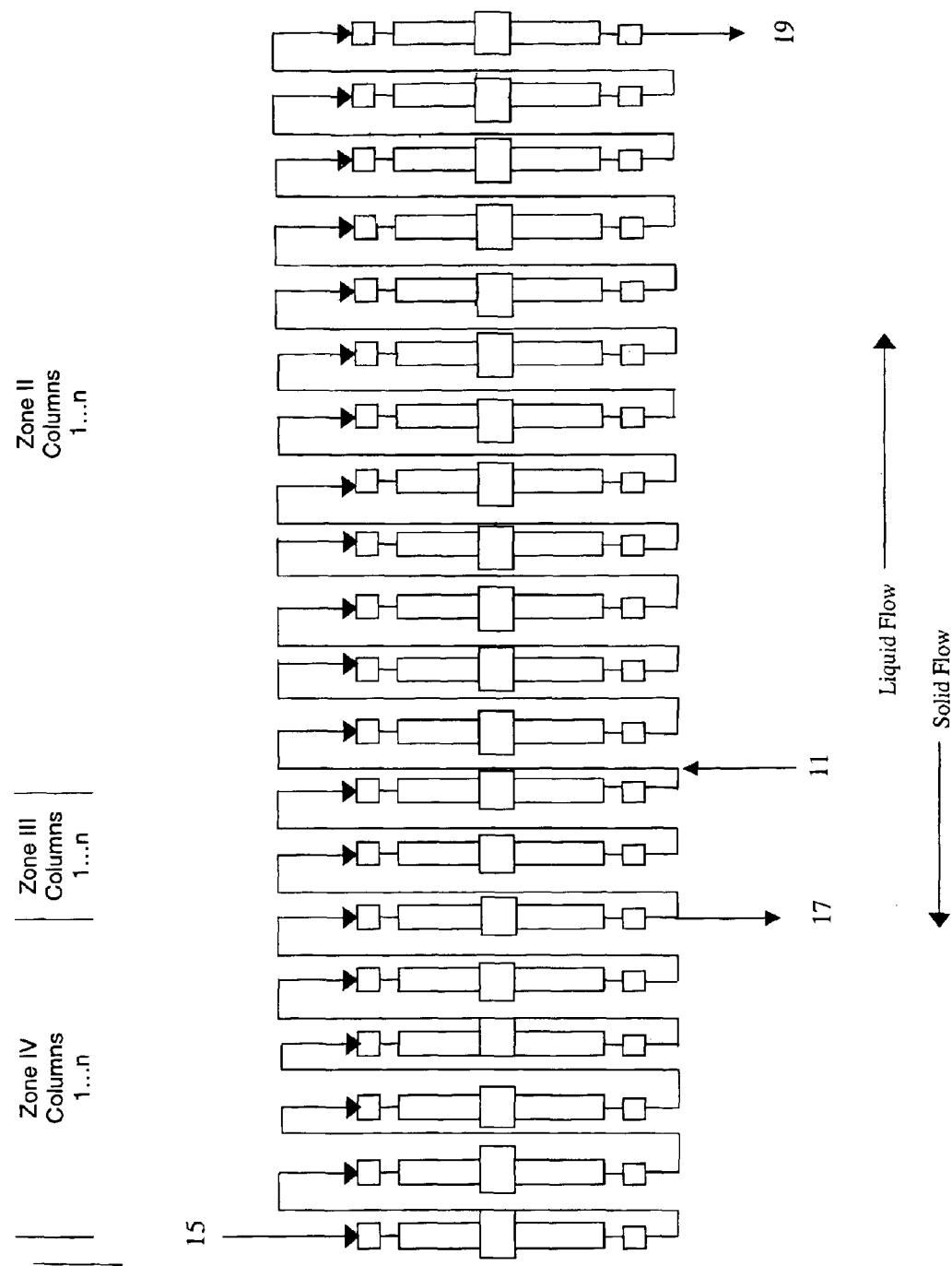
FIG. 1 shows a schematic representation of the present invention using a traditional series configuration.

In an embodiment, the process uses Amberlyst 131 acid catalyst resin. An eluent, phenol, is introduced at inlet 15, as shown in FIG. 1, for the purpose of desorbing water from the resin. A portion of the extract product at outlet 17 is pumped through the reaction zone to provide the fluid flow in this part of the unit; The acetone is fed into the system at inlet 11. A higher feed rate results in higher productivity with lower purity and a lower feed rate results in lower levels of impurities with lower productivity. In any given case, the acetone feed rate is adjusted to meet the needs of the producer. In this case, the acetone feed rate is adjusted to give a mole ratio of phenol to acetone in the range of 6:1 to 20:1. In other examples, the ratio is in the range of about 8:1–15:1, or at 12:1. The process is conducted at temperature ranges from 50° C. to 100° C. Other examples conduct the process in the range of 60° C.–90° C., or at 70° C.

In an embodiment, the invention is used in combination with a continuous liquid-solid contacting device. Continuous liquid-solid contacting devices generally strive to move a liquid phase in counter current contact with a solid phase through various means. A general review of the devices can be found in U.S. Pat. No. 5,676,826, which is incorporated herein by reference. Although any of these devices can be used with the present invention, preferred devices include those disclosed in U.S. Pat. Nos. 5,676,826; 4,808,317; 4,764,276; 4,522,726 and 6,431,202. U.S. Pat. No. 6,431,202 is incorporated herein by reference. In an example, the process is conducted in a device packed with media moving by indexing of the columns in a manner that takes place so quickly as to be considered continuous. In an example, the process utilizes a device having one control valve to conveniently utilize multiple beds, rather than many traditional SMB systems that employ multiple valve control.

The examples set forth below demonstrate the process for continuously producing BPA by condensation of acetone with phenol. One skilled in the art would appreciate that these are only set forth to be as demonstrative and various modifications may be employed that are still within the scope of the invention.

EXAMPLE 1

Continuous Fixed Bed Column

A column that is 2.5 cm in diameter and 200 cm in length was packed with 522 grams (dry weight) of a strong acid ion exchange resin. Specifically, Amberlyst 131 from Rohm & Haas was used. Such resins are also available from Dow, Bayer, and Mitsubishi, among others. The column was fed with a 12:1 mole ratio of phenol/acetone at a rate of 1.84 mls/min. The temperature was held constant at 70° C. At steady state, BPA was being continuously produced at an acetone conversion level of 81%. BPA content was determined by high performance liquid chromatography (HPLC). BPA was produced at a rate of 285 mg/min. The results are shown in Table 1.

EXAMPLE 2

High Performance Carousel SMB Complete Series Flow

The following example illustrates one of the benefits of using a traditional SMB series flow configuration with the present invention over the continuous fixed bed system of Example 1. In particular, Calgon Carbon Corporation's HPC-SMB was used. The process and advantages are not limited to such apparatus. Using the HPC-SMB packed with Amberlyst 131 resin from Rohm & Haas, phenol was reacted with acetone to produce BPA.

In this example, the unit contains a set of 20 columns that are each 1.1 cm in diameter and 30 cm in length. Each column contained 11.8 grams (dry weight) of Amberlyst 131 resin. As illustrated in FIG. 1, the elution zone (Zone IV) contains 6 columns, the enrichment zone (Zone III) contains 2 columns, and the reaction zone (Zone II) contains 12 columns. The unit is contained in an enclosure maintained at a constant temperature of 70° C. Phenol was fed into the elution zone at inlet 15 at a rate of 13.00 mls/min. The phenol moves into the enrichment zone at a rate of 2.25 mls/min which was drawn off at outlet 17. The acetone is fed at a rate of 0.150 mls/min to the reaction zone at feed inlet 11 where a condensation reaction with phenol occurs to form BPA. The strongly adsorbed water is continuously carried out of the reaction zone and into a water election zone by a counter current movement of the resin catalyst against the flow of reactants. In the water elution zone, adsorbed water is removed from the resin with the phenol at outlet 17. Enough makeup phenol is added at intake 15 to the elution zone to both dehydrate the resin and to provide enough excess phenol for the reaction zone.

At the end of the reaction zone, the crude BPA product as well as excess phenol were extracted from the process at outlet 19. A portion of the extracted product can optionally be passed to a reload zone to recover some of the phenol for re-use. This example illustrates the improvement in productivity.

The product compositions were determined using high performance liquid chromatography (HPLC). Table 1 shows a comparison of the results obtained from this example of the series flow configuration where the productivity was increased three-fold.

TABLE 1

|  | Fixed Bed Reactor | HPC-SMB |
| --- | --- | --- |
| Mole Ratio Phenol:Acetone | 12:1 | 12:1 |
| Temperature ° C. | 70 | 70 |
| Resin Catalyst | Amberlyst 131 | Amberlyst 131 |
| Total Dry Catalyst Weight g | 522 | 236 |
| % Acetone Conversion | 81 | 80 |
| Total BPA Produced mg/min | 285 | 382 |
| Productivity mg BPA/min/g dry catalyst | 0.546 | 1.62 |

EXAMPLE 3

High Performance Carousel SMB Partial Parallel Flow

Figure 2:
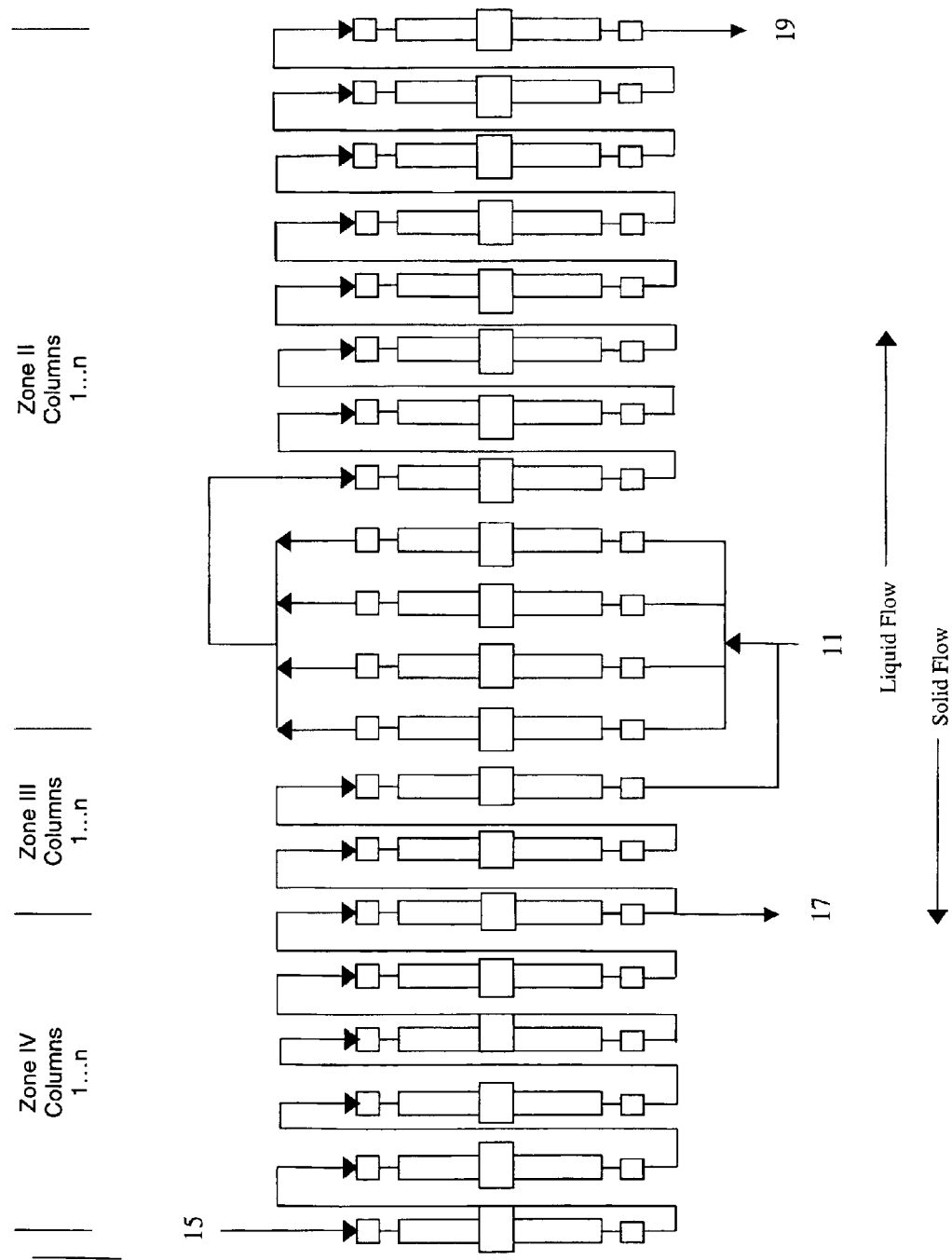
FIG. 2 shows a schematic representation of an embodiment of the present invention that combines a series flow configuration with a parallel flow configuration that uses a reverse flow mode.

The following example illustrates just one of the benefits of using a non-SMB flow configuration of the present invention with a fluid-solid contacting system. This example uses an enclosed unit containing the same number and volume of columns arranged in similar zones as used in Example 2. The concentrations, feed rates, resin, and temperature were also the same as in Example 2. As illustrated in FIG. 2, for this example the first 4 columns in the reaction zone are connected in a parallel flow configuration and the remaining 8 columns are arranged with the series flow configuration. The parallel flow columns are also run in the reverse flow mode (up-flow). This allows for an improved distribution of reactants and products that increases the yield of the BPA product while reducing the level of impurities. The product compositions were determined using high performance liquid chromatography (HPLC)I. Table 2 shows a comparison of the results obtained from this example of combining series flow and (partial) parallel flow/reverse flow configurations.

TABLE 2

| | Phenol free composition of products | | |
| --- | --- | --- | --- |
| | BPA wt % | Impurities wt % | % Acetone Conversion |
| Series Flow | 92.0 | 8.0 | 80 |
| Parallel Flow | 93.5 | 6.5 | 80 |

By contrast to this example 3, use of the traditional SMB flow configuration requires that all of the columns be connected in a series flow configuration, as shown in FIG. 1. In an embodiment, the present process, as illustrated in Example 3, combines series, parallel and reverse flow configurations together in one unit in the reaction zone to advantageously improve BPA yield, reduce impurities, and prevent pressure build up in the columns. It is also not limited by the number of columns used in a zone and the zones are established based upon the process objectives.

While the foregoing has been set forth in considerable detail, the examples and methods are presented for elucidation and not limitation. It will be appreciated from the specification that various modifications of the invention and combinations of elements, variations, equivalents, or improvements therein may be made by those skilled in the art, and are still within the scope of the invention as defined in the appended claims.

What is claimed is:

1. A process for the continuous production of bisphenol-A in a plurality of selectable columns comprising:
   (a) continuously inputting phenol into an inlet of at least one column for accepting a fluid flow, each of said columns accepting phenol containing an acid catalyst resin and having at least one inlet for accepting a fluid flow and at least one outlet for discharging said flow to at least one other column or a combination of columns; each said column being selectively connected to one or more of said other columns in an up-flow or down-flow mode wherein at least two of said inlets can selectively create a parallel flow and wherein some but not all said columns are connected in series having a unidirectional flow;
   (b) inputting acetone into said at least one inlet of at least one said column accepting phenol; and
   (c) flowing said phenol with said acetone over said acid catalyst resin to form bisphenol-A and water, and continuously or essentially continuously removing said water from said reaction.

2. A process as set forth in claim 1 wherein said acid catalyst resin is provided in a carousel simulated moving bed reactor.

3. A process as set forth in claim 1 wherein said acid catalyst resin is an ion exchange resin.

4. A process as set forth in claim 1 further including the step of inputting an eluent into said at least one inlet of at least one said column.

5. A process as set forth in claim 4 wherein said eluent is phenol.

6. A process as set forth in claim 2 wherein the mole ratio of phenol to acetone is in the range of about 6:1–20:1.

7. A process as set forth in claim 2 wherein the process temperature is in the range about 5–100° C.

8. A process as set forth in claim 2 wherein at least one second column or bed in said reactor is configured to have a reverse flow wherein said fluid flows in a direction opposite to said flow in said at least one column or toward the top of the column, or both.

9. A process as set forth in claim 1 further including the step of removing said water from said at least one outlet of at least one said column.

10. A process as claim 9 wherein set forth in said step of removing said water is conducted simultaneously or sequentially as said solvent reacts with said acetone.

11. A process as set forth in claim 9 wherein said step of removing said water is conducted continuously or essentially continuously.

12. A process as set forth in claim 1, further including an adsorbent or separation media.

13. A process as set forth in claim 1, wherein said catalyst, adsorbent, separation media or combination thereof is selected from the group consisting essentially of activated carbon, silica gels, aluminas, zeolites, zirconias, titanias, silicates, diatomaceous earths, and ion exchange resins.

14. A process as set forth in claim 1, wherein at least two columns are connected to create a parallel flow to dilute said acetone or reduce formation of by-products resulting from reaction of said acetone.

15. A process as set forth in claim 1, wherein said columns are configured to have a reverse flow to release pressure buildup in said columns.

16. A process as set forth in claim 1 further including the step of flowing an eluent counter current to said resin.

17. A process as set forth in claim 1, wherein at least two columns are connected in parallel, wherein said parallel columns provide a reverse flow.

18. A process as set forth in claim 4 wherein said eluent is selected from the group consisting of alcohols, ketones, esters, aliphatic hydrocarbons, aromatic hydrocarbons, amides, nitriles, water or buffered solutions, and mixtures thereof.

* * * * *